United States Patent
Mateus Dias Quinaz (10) Patent No.: US 10,603,190 B2
(45) Date of Patent: Mar. 31, 2020

(54) JOINT ASSISTIVE AND LOCKING DEVICE

(71) Applicant: NUADA, LDA, Braga (PT)

(72) Inventor: Filipe Nuno Mateus Dias Quinaz, Guarda (PT)

(73) Assignee: NUADA, LDA, Braga (PT)

( * ) Notice: Subject to any disclaimer, the term of this patent is extended or adjusted under 35 U.S.C. 154(b) by 73 days.

(21) Appl. No.: 15/115,047

(22) PCT Filed: Feb. 2, 2015

(86) PCT No.: PCT/IB2015/050782
§ 371 (c)(1),
(2) Date: Jul. 28, 2016

(87) PCT Pub. No.: WO2015/114601
PCT Pub. Date: Aug. 6, 2015

(65) Prior Publication Data
US 2016/0361179 A1    Dec. 15, 2016

(30) Foreign Application Priority Data

Jan. 31, 2014    (PT) .......................... 107443

(51) Int. Cl.
| | | |
|---|---|---|
| *A61F 2/72* | (2006.01) | |
| *A61F 5/01* | (2006.01) | |
| *A61B 5/00* | (2006.01) | |
| *A61B 5/11* | (2006.01) | |
| *A61F 2/68* | (2006.01) | |
| *A61F 2/70* | (2006.01) | |

(52) U.S. Cl.
CPC .............. *A61F 2/72* (2013.01); *A61B 5/1107* (2013.01); *A61B 5/6806* (2013.01); *A61F 5/0118* (2013.01); *A61F 2002/6854* (2013.01); *A61F 2002/704* (2013.01); *A61F 2005/0155* (2013.01); *A61F 2005/0158* (2013.01)

(58) Field of Classification Search
CPC .... A61F 2002/6854; A61F 2/586; A61F 2/72; A61F 2005/0155; A61F 2005/0158; A61F 2002/704; A61F 5/0118; A61B 5/0118
See application file for complete search history.

(56) References Cited

U.S. PATENT DOCUMENTS

| | | |
|---|---|---|
| 1,247,077 A | 11/1917 | Caron |
| 5,538,488 A | 7/1996 | Villepigue |
| 2003/0120183 A1* | 6/2003 | Simmons .................. A61F 4/00 600/595 |

(Continued)

FOREIGN PATENT DOCUMENTS

| | | |
|---|---|---|
| EP | 2417941 A1 | 2/2012 |
| WO | 2008027002 A1 | 3/2008 |

OTHER PUBLICATIONS

International Search Report and Written Opinion for International Application No. PCT/IB2015/050782 (dated Jun. 16, 2015) (6 pages).

*Primary Examiner* — Christie L Bahena
(74) *Attorney, Agent, or Firm* — Lucas & Mercanti, LLP (57) ABSTRACT

Disclosed herein is a device for assisting and locking joints, having a supporting structure in the joint, at least one tensioning system fixed to the supporting structure and at least one artificial tendon connected to the tensioning system. The tension system interacts with the locking system in order to assist the user's joints when needed.

8 Claims, 11 Drawing Sheets

(56) References Cited

U.S. PATENT DOCUMENTS

| | | | |
|---|---|---|---|
| 2004/0059432 A1* | 3/2004 | Janusson | A61B 5/103 623/36 |
| 2012/0029399 A1* | 2/2012 | Sankai | A61B 5/04888 601/40 |
| 2013/0226350 A1 | 8/2013 | Bergelin et al. | |
| 2013/0289452 A1 | 10/2013 | Smith et al. | |

* cited by examiner

JOINT ASSISTIVE AND LOCKING DEVICE

CROSS REFERENCE TO RELATED APPLICATION

This Application is a 371 of PCT/IB2015/050782 filed on Feb. 2, 2015, which claims priority of Portuguese Application No. 107443 filed Jan. 31, 2014, both of which are incorporated herein by reference.

TECHNICAL FIELD

The present application relates to a joint assistive and locking device.

BACKGROUND ART

A human being uses the hands for a large number of activities. However, for several reasons, there is the need towards systems for assisting and supporting the function of the hands.

One of the most common reasons derives from the existence of medical conditions, such as fractures, arthritis and muscular problems, among others, which hinder or restrict the patient when using the hands for normal activities.

Another reason arises from the requirement of the task meant to be undertaken. In a situation of stress, either from professional activities or sports events, the hand may limit the performance.

Finally, the use of systems to provide assistance to the function of the hand may result in a reduction of the effort and consequent increase of comfort.

Currently, some systems provide assistance and support in some of these situations.

These may be simple systems, such as padded gloves, aiming at providing greater assistance and resistance to the hand.

They may also be more complex systems using artificial tendons, often as flexible and resilient wires, which are attached to the fingers of a glove, usually to all five fingers. In the opposite end to the finger, these artificial tendons are connected to electric motors that move, push and pull, tendons.

As these systems use motors to pull and/or push artificial tendons or structures attached to the user's finger, this means that the opening and closing range of the hand is controlled by the motor. There are several models, but all use at least one motor, typically electric.

The use of a motor to move fingers has several drawbacks.
the motor needs to be powered, typically with batteries, which not only involves a high energy consumption and the use of large batteries and/or low-powered motors but also prevents or limits the sport and everyday use of these systems;
motors, typically more than one, turn systems more expensive. These systems are complex and bulky and are used to assist medical problems mainly in medical centers. Some use backpacks to integrate the components, are very expensive systems, and are also incompatible with the normal use of the hand.

In practice, hand support systems are complex, cumbersome and add volume which prevents the normal use of the hand.

The following documents disclose some prior art solutions.

U.S. Pat. No. 5,538,488 discloses a glove to exercise the fingers, within which, supports for the tips of each finger are provided.

The invention comprises several cables tensioned with springs and, by means of an adjustment system, it allows creating the desired resistance to the closing movement of the hand. The glove is fixed by means of a wrist strap.

The glove referenced in this document aims only at exercising the fingers. Thus, tensioned cables shall solely act in order to exert an adjustable force on the fingers.

EP2417941A1 discloses a glove for movement assistance which includes a portion for the insertion of fingertips and linear elements along the fingers which are configured from a mechanism for transmitting the force required for the extension or contraction movement of the fingers. The solution also includes a component for detecting biological signals that are used by the control component and a data display.

This document focuses on how the motor operates on the elements arranged in the glove fingers. The fact that it needs an electrical motor to pull or push the elements placed in the glove fingers translates in an elevated power consumption and a reduced limit of the exerted force. Additionally, due to the existence of these elements in the fingers, the glove will always be more voluminous, less discreet and more intrusive in the user activities.

WO2008/027002A1 discloses a glove used for strengthening the hand grip movement which includes the fingers of the glove containing an artificial tendon on each side extending along the inner side of the glove, a support on the fingertip, a strength detection sensor, actuators and a control unit determining the strength exerted on the artificial tendons based on the strength detected by the sensor thus leading the finger to bend.

This document focuses primarily on how the wires pass through the glove, since disclosing a motor that pulls the wire corresponding to the finger in order to assist the movement of the finger.

In general, systems known in the art act on the user's limbs, in some cases actively moving the user's fingers.

SUMMARY

The present application discloses a joint assistive and locking device, comprising:
a support structure in the joint;
at least one tensioning system, fixed to the support structure;
a locking system comprising a movable part which engages the tensioning system; and
at least one artificial tendon connected to the tensioning system.

In one embodiment, the tensioning system comprises springs or metal bands. In another embodiment, the circular tensioning system comprises a sprocket. In yet another embodiment, the linear tensioning system comprises a wire structure with cones.

In one embodiment, the locking system further comprises: a locking actuator; an electronic circuit board; at least one sensor; and a battery. In another embodiment, the device further comprises a digital display.

In yet another embodiment, the device further comprises at least a measuring device of the following biological signs: heart rate; blood pressure; among others In one embodiment, the device further comprises at least one artificial tendon pressure sensor.

The present application further discloses a method of operating a locking system configured to implement the steps of:
  obtaining a measurement from at least one sensor;
  activating the locking actuator, if the muscle electrical signal measured correlates with the closing of the joint; and
  deactivating the locking actuator, if the muscle electrical signal measured correlates with the opening of the joint.

The present application discloses a method of operating a locking system configured to implement the steps of:
  obtaining a measurement from at least one artificial tendon pressure sensor; and
  unlocking the locking system, if the system is subject to excessive pressure.

DISCLOSURE OF INVENTION

The present application arises from the need to actively and dynamically assist joint function with low power consumption, small volume and light weight.

The locking and unlocking electronic system, since being simple and mostly mechanical, has an extremely low power consumption. This allows size reduction of batteries or other power systems.

The solution assists a decrease on the strength required to keep the joint in a static position, thus hindering an unwanted opening thereof.

The system may be slightly different depending on the purpose thereof. Thus, the same functionality may be applied to joints, for example the elbow, shoulder, back, adapting for each case the shape but maintaining the function of the assistive system. The present solution mainly focus in the position locking of the user's hand.

Since the system assists at maintaining the natural position of the user's joint, there is no need for motors or actuators to move the fingers. Thus, in practice, there is a considerable decrease on the weight, size and cost of the device compared to existing solutions.

Since being much smaller than other solutions, it allows the incorporation of the systems herein described, for example, in a glove and support incorporated in the forearm.

The system may be produced with a manual locking system, another solution with this capability not being known in the market. The manual locking system may be replaced or accompanied by an electronic lock control system.

The system herein described has several advantages since being simple and easy to produce. This simplicity is made possible by the understanding of the problems meant to be solved, wherein no specialized solution has been provided.

The present solution operates through a different model from that of known prior art solutions. Instead of having a motor pulling or pushing the user's fingers, the present solution mainly locks the fingers whenever desired by the user, the hand being held in the desired position, thus resisting external opening forces.

Opening and closing of the hand depend on the user's hand muscles.

In this solution, sensors and motors are intended to lock or unlock a mechanical system. This feature is not observed in any solution known in the art.

Prior art solutions are different since some are not useful for other functions besides that of exercising a human joint, unlike the present solution which aims at locking the opening of the user's joint in a particular position in order to, for example, assist holding objects. Other solutions neither have a locking system, nor means of monitoring the hand function.

Still other prior art solutions do not provide the possibility of locking only fingers and prevent them from moving as disclosed in the present application, some of such solutions involving the use of actuators that push and pull the user's joint. In addition, some prior art solutions detect motion by processing a biosignal, not providing flexion and pressure sensors such as those disclosed in the present application.

In the present solution no movement is exercised through motors controlling wires. This movement is made mechanically, to which a locking system is added, which may be automatic or manual. In practice, the use of elements which may be considered as actuators is not necessarily observed.

The present solution may be used for medical reasons by patients who maintain the opening and closing function of the hand, regardless of strength. Additionally, it may be used for sports, professional and everyday life purposes.

BRIEF DESCRIPTION OF DRAWINGS

For an easier understanding of the present application drawings are herein attached, which represent preferred embodiments which, however, are not intended to limit the technique herein disclosed.

FIG. 7 shows an embodiment of a manual locking system, wherein reference numbers represent:

701—tensioning system; and

702—locking button or lever.

FIG. 8 shows an embodiment of a digital display system wherein reference numbers represent:

404—fixing system for arm support;

702—locking button or lever; and

801—digital display (in this case, arranged under the top cover of the tensioning system).

FIG. 9 shows an embodiment of a manual locking system with linear tensioning system, wherein reference numbers represent:

102—artificial tendon;

402—movable part of the locking system;

702—locking button or lever;

901—connection between the artificial tendon and tensioning system; and

902—linear tensioning system.

FIG. 10 shows an embodiment of part of a linear tensioning system, wherein reference numbers represent:

402—movable part of the locking system; and

403—sprocket (ratchet) teeth engaged with a linear system.

FIG. 11 shows an embodiment of part of a linear locking system, wherein reference numbers represent:

402—movable part of the locking system;

601—support for the hand and arm with arm adjustment; and

702—locking button or lever.

BEST MODE FOR CARRYING OUT THE INVENTION

Referring to the figures, some embodiments shall now be described in more detail, which are not however intended to limit the scope of the present application.

The following embodiment is particularly suitable to increase the strength with which the hand is maintained in a closed position.

Figure 1:
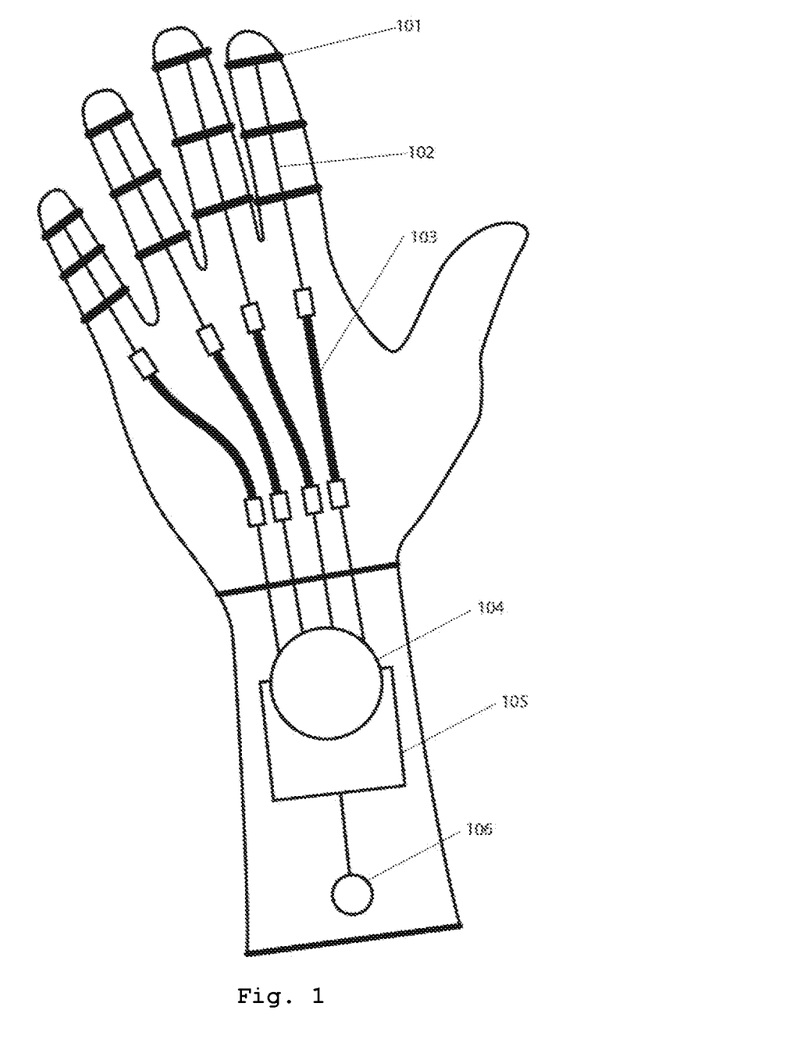
FIG. 1 shows an embodiment of the present solution, wherein reference numbers represent:
  101—artificial tendon support;
  102—artificial tendon;
  103—non-compressible artificial tendon support;
  104—tensioning system;
  105—locking system; and
  106—muscle signal sensor.
Figure 2:
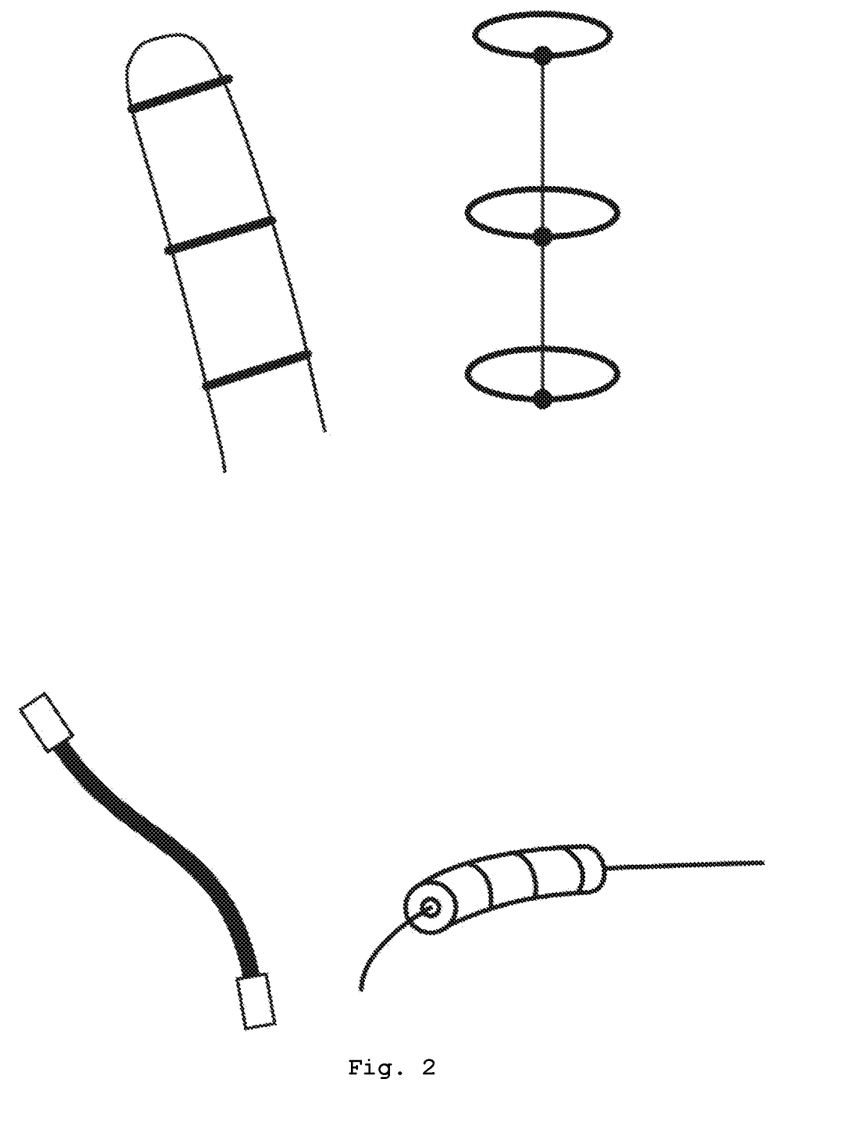
FIG. 2 shows an embodiment of a support system of artificial tendons.
Figure 6:
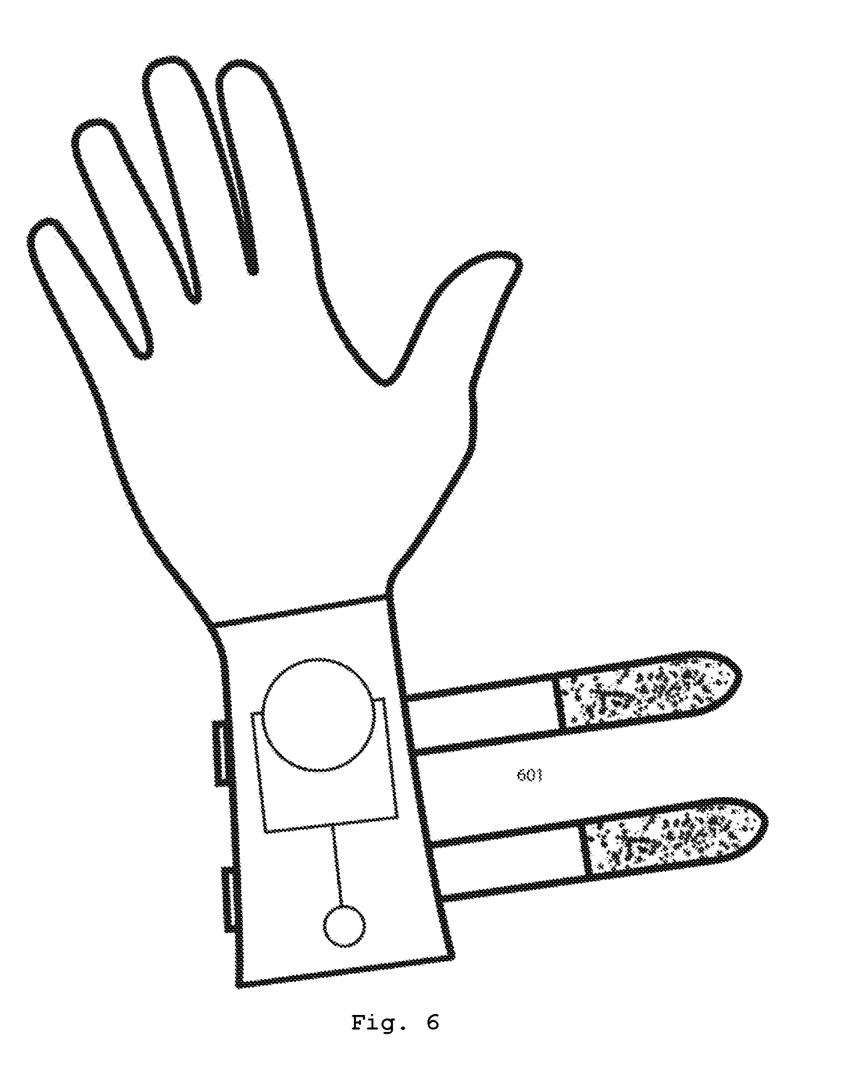
FIG. 6 shows an embodiment of a supporting system, wherein reference numbers represent:
  601—support for the hand and arm with arm adjustment.

In one embodiment, the present solution comprises a support structure for the user's hand and arm, wherein a glove establishes the connection between fingers and artificial tendons, one for each finger, held by the tendon supports.

These tendons may be flexible and resistant wires which cause the hand to close when the arm is stretched and they are pulled towards the body alongside the arm.

Figure 3:
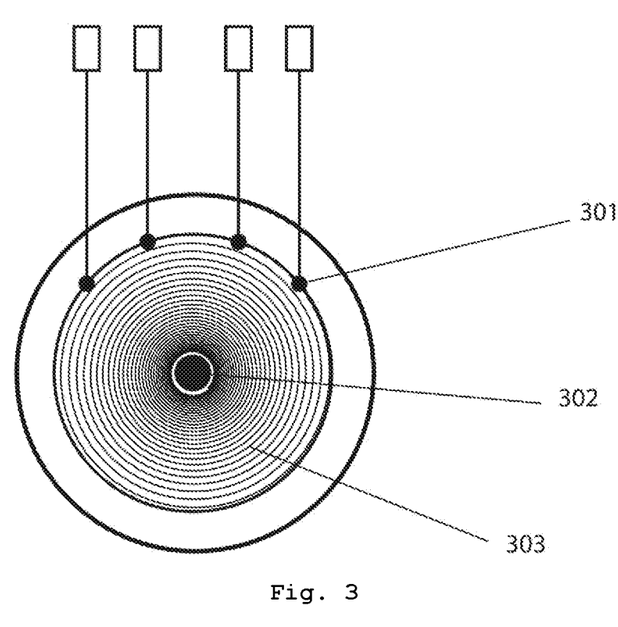
FIG. 3 shows an embodiment of the tensioning system, wherein reference numbers represent:
  301—connection of artificial tendons to the rotary tensioning system;
  302—fixed axle connecting the rotary system to arm support; and
  303—movable part of the mechanical tensioning system (spring system providing tension).

These tendons are connected to at least one tendon tensioning system located in the arm. In the simplest case, when only one tensioning system is present, all tendons are connected thereto. When one tensioning system is provided for each finger, each artificial tendon is connected to its respective tensioning system. The existence of multiple tensioning systems allows the present solution to assist the opening strength resistance with the fingers in different positions. As opposed to this solution, when all fingers are connected to the same tensioning system, locking the tensioning system involves maintaining all fingers in the same position there between.

When the user closes the hand, the minimum distance between the tip of the fingers and the wrist decreases. By decreasing, since artificial tendons (which may be wires) follow the movement of the fingers, the tensioning system collects the excess. The tensioning system may be a circular or linear system. The operation thereof is based on springs, metal bands or other options that cause a small retraction force to be applied onto the tendons towards the wrist.

The tensioning system has a movable part, which undertakes linear or circular movements, connected to the tendons, and a fixed part of the support structure located in the arm.

Figure 4:
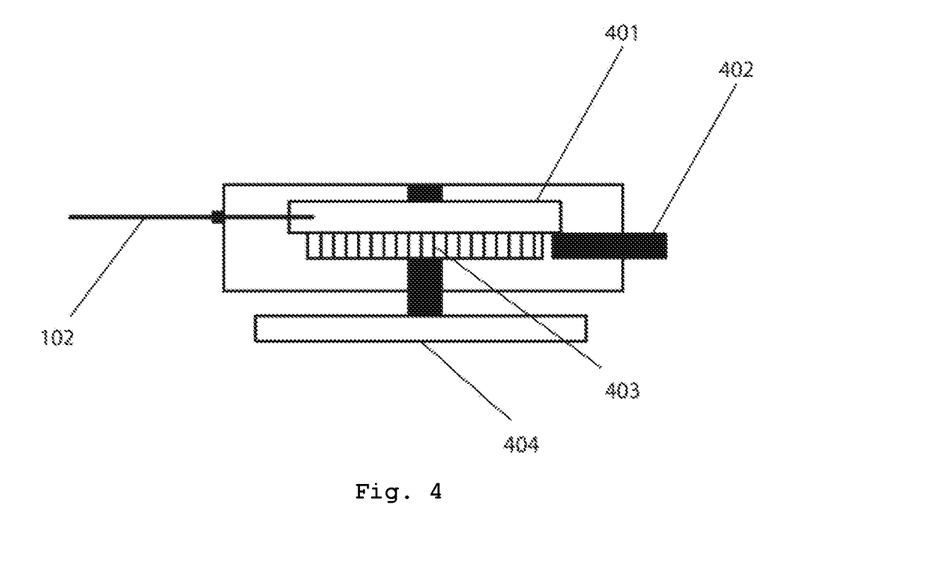
FIG. 4 shows an embodiment of the tensioning system with components of the locking and supporting system, wherein reference numbers represent:
  102—artificial tendon;
  401—rotary tensioning system;
  402—movable part of the locking system;
  403—sprocket (ratchet) fixed to the rotary system; and
  404—fixed support axis base.

The movable part of the circular tensioning system is fixed to a sprocket which is in turn connected to the locking system.

When the locking system is locked, the movable part of the tensioning system moves freely in closed hand movement, but locks the opening movement.

When the locking system is unlocked, the movable part of the tensioning system moves freely.

Figure 7:
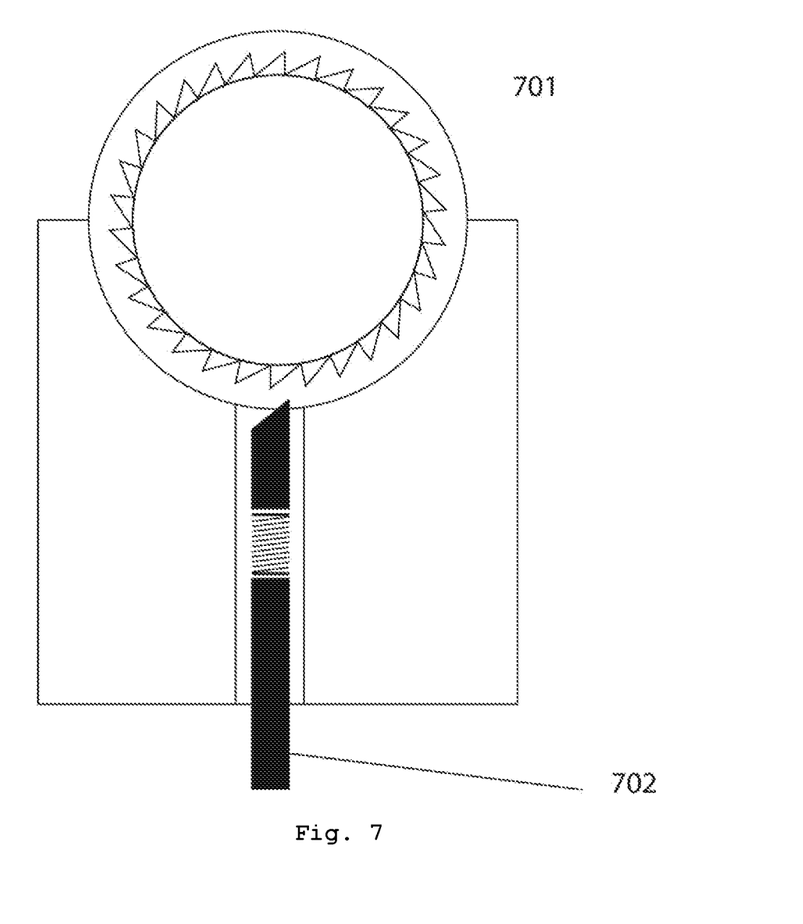

The manual circular system comprises a movable part which engages the sprocket, preferably a ratchet fixed to the circular tensioning system, in a supporting system and a spring.

Figure 5:
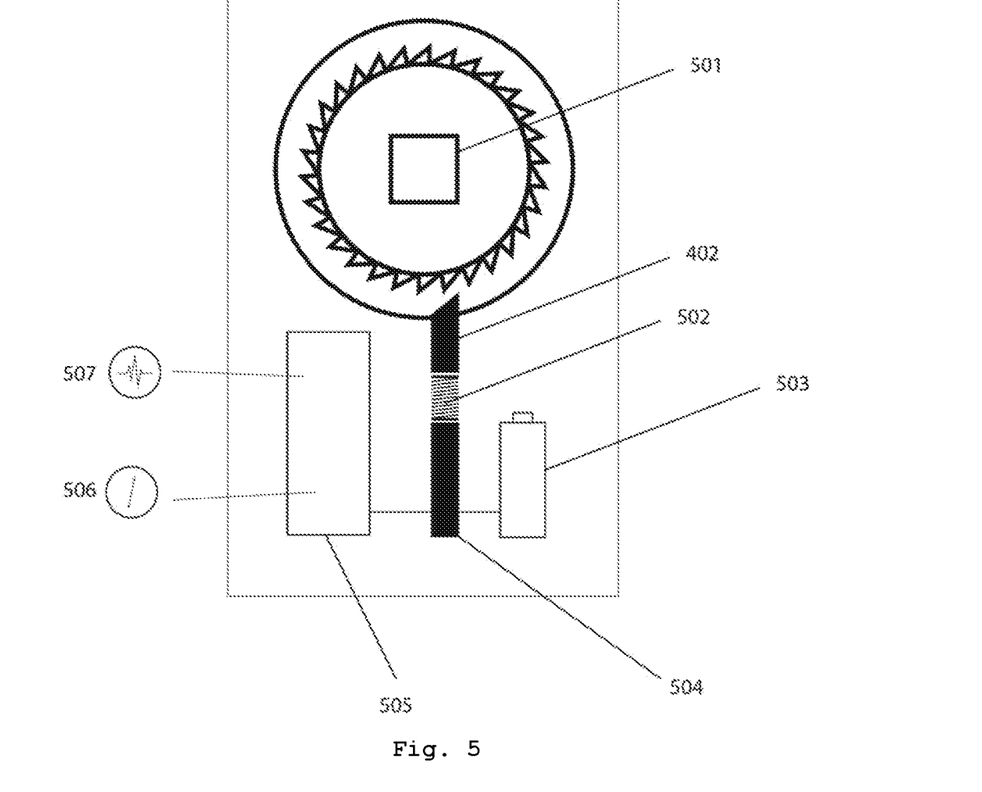
FIG. 5 shows an embodiment of an electronic locking system, wherein reference numbers represent:
  402—movable part of the locking system;
  501—tendon pressure sensor;
  502—spring;
  503—battery;
  504—electric actuator;
  505—circuit board;
  506—muscle electrical signal reader; and
  507—biological signal reader.

In one embodiment, the locking system of the position of the tendons may be electronic, comprised by the components of the manual system accompanied by a locking actuator, an electronic circuit board, at least one sensor and a battery.

It is the displacement of the movable part of the tendon position locking system that causes the system to lock. The manual displacement of the movable part may be controlled by the user. The electronic displacement is made with an electrical actuator powered by a battery. Locking or unlocking the electronic system is controlled manually or by processing the sensor signal. There are different electrical signals associated with opening and closing of the hand. They have been widely disclosed, and there are commercially-available sensors to detect them. Whenever the sensor is sending electrical signals associated with the closing of the hand, the system is locked (locking the system allows closing the hand, but not opening it). If the sensor sends electrical signals associated with the opening, the system is unlocked and the user can open the hand.

When the system is locked the movable part of the locking system is in contact with the sprocket of the circular tensioning system.

There is a spring which causes the movable part of the circular locking system to move when the sprocket of the circular tensioning system pivots in one direction but does not allow the displacement thereof in the opposite direction (thus locking the system).

The movable part of the electronic locking system is connected to a locking actuator. This actuator is a small electrical device, connected to a battery and a circuit board that causes the movable part to move in order to lock the system.

The actuator is connected to a circuit board. This board processes system information in order to lock or unlock the system according to the present specification. It interprets information from muscle electrical signal sensors, from the pressure and flection sensors in the finger, artificial tendon pressure sensors or biological variable sensors. It may unlock the system if, for example, the pressure on the tendons is too high.

The muscle electrical signal sensors, at least one, is positioned in the arm and is connected to the circuit board mentioned above.

There is at least one tendon pressure sensor located in the glove or arm and is connected to the circuit board.

The pressure and flection sensors in the fingers, are located in the user fingers and allow to identify signals associated with the closing and opening of the hand.

The biological variable sensors enable the measurement of heart rate, blood pressure, among others. These features depend on the sensor subsequently chosen. These sensors are sensors already available in the market, and therefore we shall only describe its incorporation into the system. This feature may not be present in all models of the present invention. These sensors are connected to the circuit board.

Figure 8:
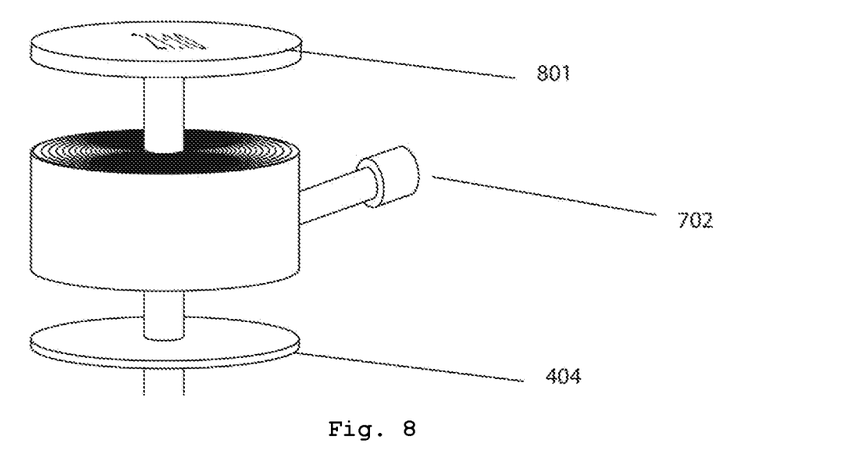
Figure 9:
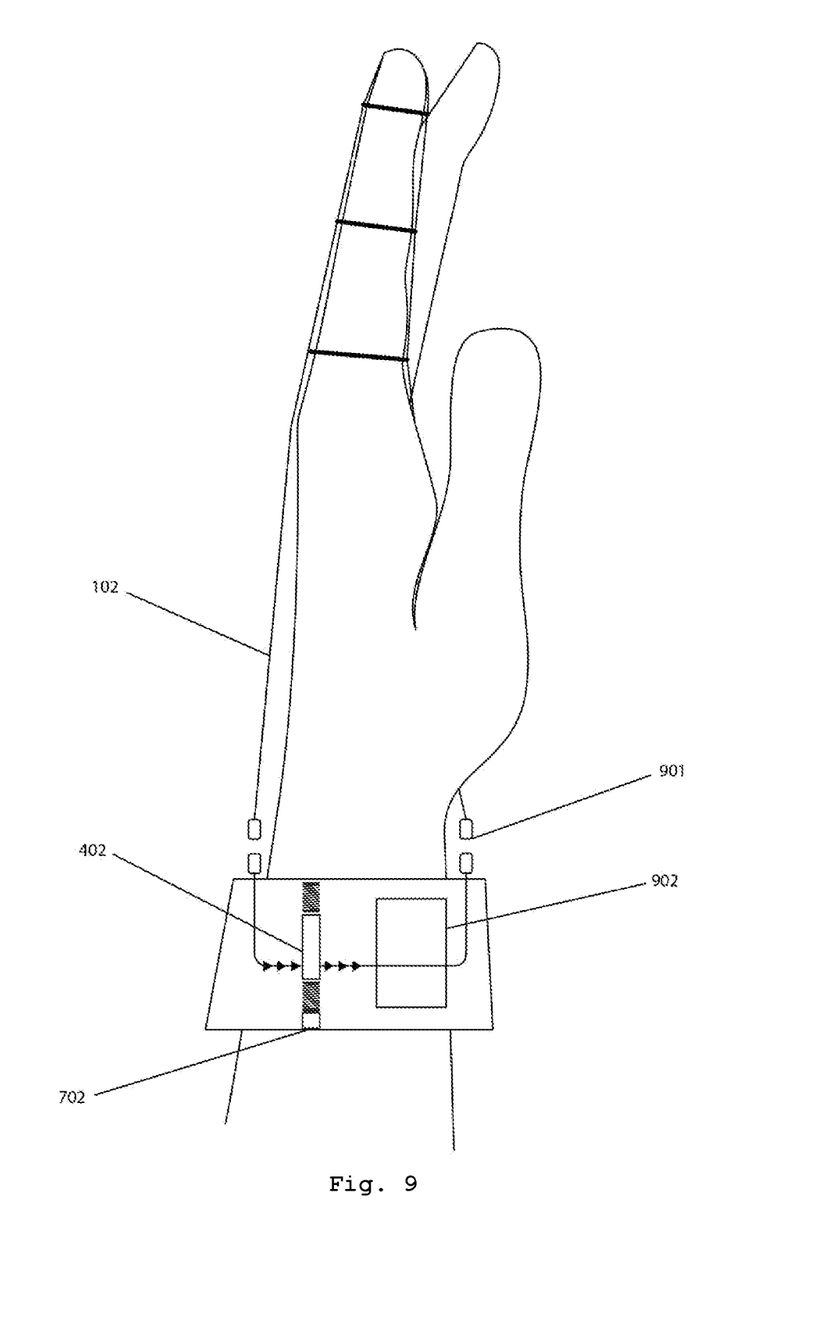
Figure 10:
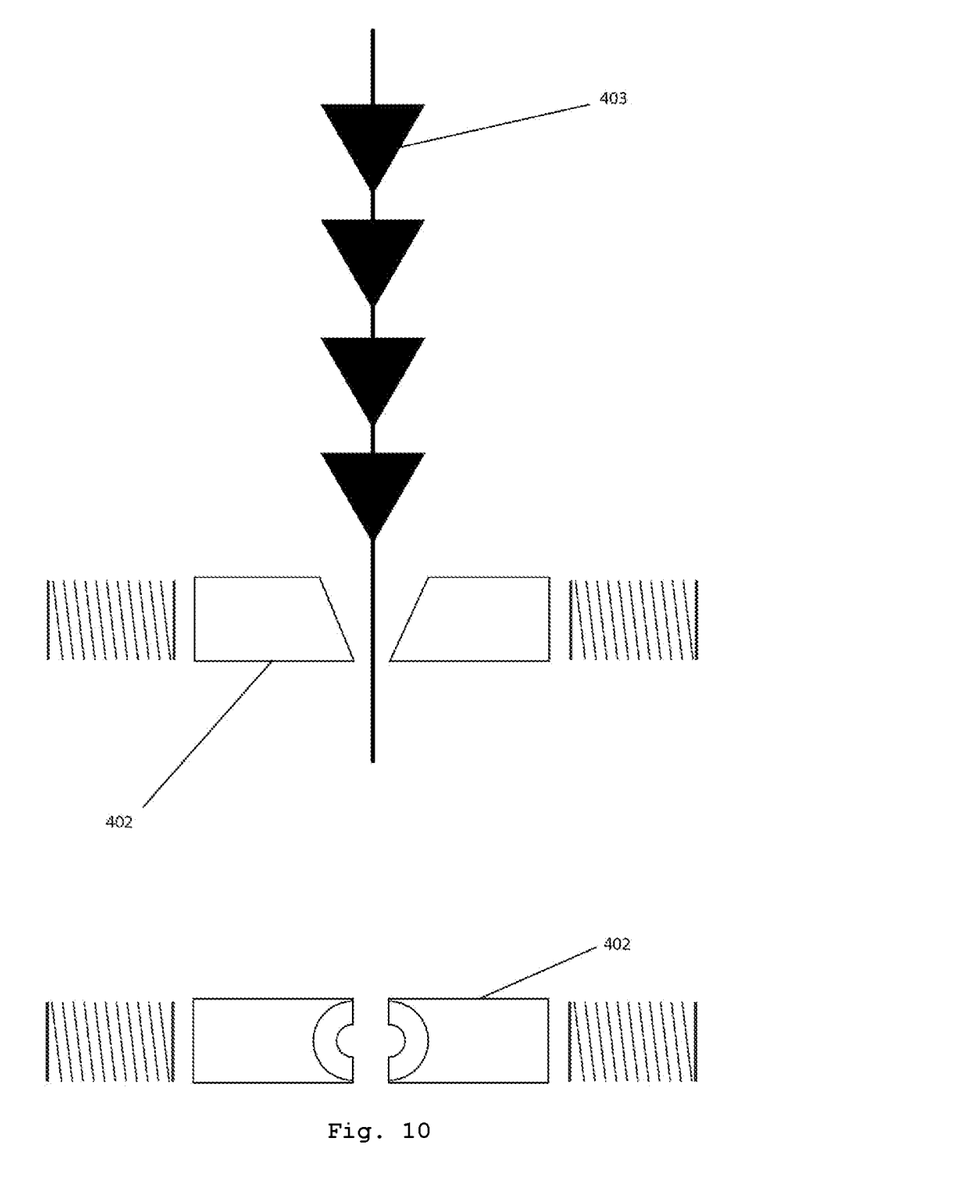
Figure 11:
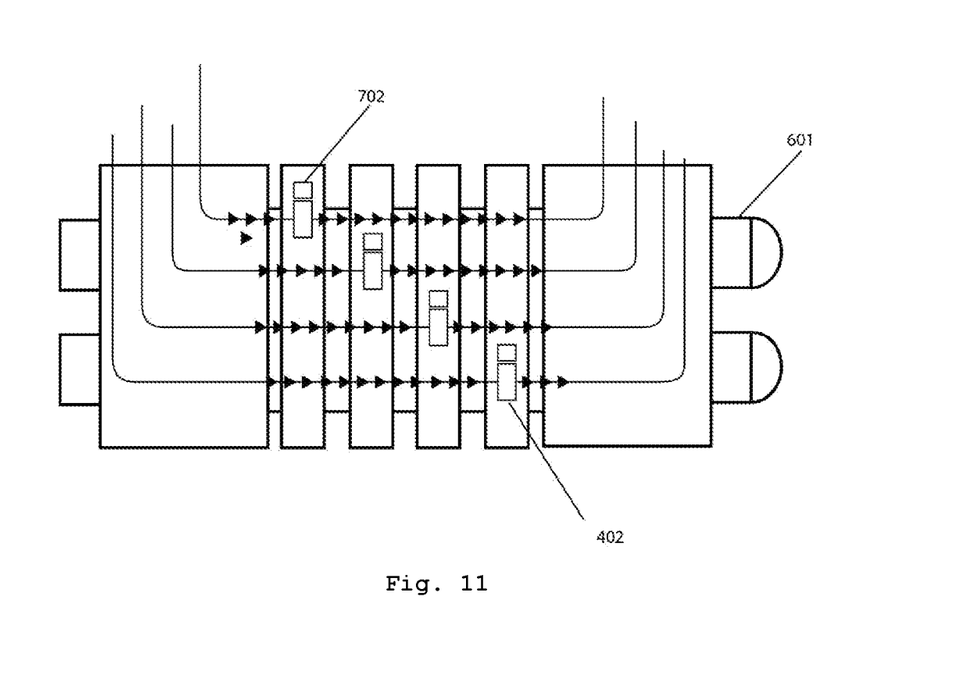

Finally, the information obtained by all described components, or the information provided by the circuit board, may be displayed on a digital display.

In one embodiment, the device comprises a digital screen allowing the information to be displayed.

In another embodiment, the device described is accompanied by biological signal meters, such as heart rate, blood pressure, among others. These measurements are displayed on the system screen.

Finally, another variation of the present use allows incorporating artificial tendon pressure sensors, thus allowing the system to be unlocked when subject to excessive pressures. The pressure display can be looked up in the system screen.

This embodiment relates to a hand function assistive system that is based on locking the movement of artificial tendons in a unidirectional manner.

The system locks, on request, the artificial tendon, which follows the user's finger during hand movement.

This means that the user may allow the artificial tendon to withstand an external force that would cause the hand to open, carrying weights, pulling objects, picking up objects, or others.

The present disclosure is of course in no way restricted to the embodiments herein described and a person of ordinary skill in the art will be capable of providing many modification possibilities without departing from the general idea of the invention as defined in the claims. The embodiments described above are obviously combinable with each other. The following claims define further preferred embodiments.

The invention claimed is:

1. A joint assistive and locking device for a hand, comprising:
   a support structure adapted to fit on a wrist of a user;
   at least one artificial tendon adapted to extend along a length of a respective finger;
   at least one artificial tendon support adapted to be attached to the respective finger and to the at least one artificial tendon;
   at least one mechanical tensioning system disposed in the supporting structure, the at least one mechanical tensioning system being coupled to the at least one artificial tendon, the at least one mechanical tensioning system having no motor, the at least one mechanical tensioning system comprising a device of a type that uses only mechanical energy, the at least one mechanical tensioning system being adapted to store mechanical energy in a first movable part and use the mechanical energy stored in the first movable part to cause the at least one artificial tendon to move;
   a sprocket attached to the first movable part of the at least one mechanical tensioning system, the sprocket having a plurality of teeth; and
   a locking system comprising a second movable part adapted to move between an unlocked position in which the second movable part is not in contact with the sprocket and a locked position in which the second movable part is in contact with the sprocket.

2. The device according to claim 1, wherein the at least one tensioning system comprises metal bands.

3. The device according to claim 1, wherein the locking system further comprises:
   at least one sensor disposed on a body part of the user, the at least one sensor being adapted to generate information relating to one of a movement, a pressure, and a biological signal; and
   a locking actuator comprising an electronic circuit board and a battery, the locking actuator being adapted to:
      receive the information from the at least one sensor; and
      cause the second movable part to move between the unlocked position and the locked position, based on the information.

4. The device according to claim 3, wherein the locking actuator is configured to:
   obtain a measurement of an electrical signal associated with a movement measured by the at least one sensor;
   cause the second movable part to move to the locked position, if the electrical signal correlates with a first predetermined movement of the hand or wrist; and
   deactivate the locking actuator cause the second movable part to move to the unlocked position, if the electrical signal correlates with a second predetermined movement of the hand or wrist.

5. The device according to claim 1, further comprising a digital display.

6. The device according to claim 1, further comprising a measuring device adapted to measure one of a heart rate or a blood pressure.

7. The joint assistive and locking device of claim 1, wherein:
   the mechanical energy used by the at least one tensioning system is provided by a user.

8. A joint assistive and locking device, comprising:
   a support structure adapted to fit on a joint of a user;
   at least one artificial tendon adapted to extend along a length of a selected body part of the user;
   at least one artificial tendon support adapted to be attached to the respective selected body part and to the at least one artificial tendon;
   at least one mechanical tensioning system disposed in the supporting structure, the at least one mechanical tensioning system being coupled to the at least one artificial tendon, the at least one mechanical tensioning system having no motor, the at least one mechanical tensioning system comprising a device of a type that uses only mechanical energy, the at least one mechanical tensioning system being adapted to store mechanical energy in a first movable part and use the mechanical energy stored in the first movable part to cause the at least one artificial tendon to move;
   a sprocket attached to the first movable part of the at least one mechanical tensioning system, the sprocket having a plurality of teeth; and
   a locking system comprising a second movable part adapted to move between an unlocked position in which the second movable part is not in contact with the sprocket and a locked position in which the second movable part is in contact with the sprocket.

* * * * *